United States Patent
Dobak, III

[11] Patent Number: 6,149,677
[45] Date of Patent: *Nov. 21, 2000

[54] CIRCULATING FLUID HYPOTHERMIA METHOD

[75] Inventor: John D. Dobak, III, Del Mar, Calif.

[73] Assignee: Innercool Therapies, Inc., San Diego, Calif.

[*] Notice: This patent is subject to a terminal disclaimer.

[21] Appl. No.: 09/306,865

[22] Filed: May 7, 1999

Related U.S. Application Data

[62] Division of application No. 09/052,545, Mar. 31, 1998.

[51] Int. Cl.$^7$ ........................................................ A61F 7/00
[52] U.S. Cl. ........................... 607/106; 607/104; 607/105; 606/20
[58] Field of Search ..................... 604/113, 43, 264, 604/280; 607/96, 104–107, 113, 114; 606/20, 21, 22; 128/898

[56] References Cited

U.S. PATENT DOCUMENTS

| | | |
|---|---|---|
| 2,308,484 | 1/1943 | Auzin et al. ................................. 18/58 |
| 2,374,609 | 4/1945 | McCollum . |
| 2,615,686 | 10/1952 | Davidson . |
| 2,672,032 | 3/1954 | Towse ....................................... 62/126 |
| 2,913,009 | 11/1959 | Kuthe . |
| 3,298,371 | 1/1967 | Lee . |
| 3,425,419 | 2/1969 | Dato . |
| 3,504,674 | 4/1970 | Swenson et al. ...................... 128/303.1 |
| 3,865,116 | 2/1975 | Brooks ..................................... 128/400 |
| 3,888,259 | 6/1975 | Miley ....................................... 128/400 |
| 3,971,383 | 7/1976 | van Gerven . |
| 4,038,519 | 7/1977 | Foucras ..................................... 219/301 |
| 4,153,048 | 5/1979 | Magrini .................................... 128/692 |
| 4,190,033 | 2/1980 | Foti ......................................... 128/742 |
| 4,231,425 | 11/1980 | Engstrom ................................ 165/156 |
| 4,275,734 | 6/1981 | Mitchiner .............................. 128/303.1 |
| 4,298,006 | 11/1981 | Parks ....................................... 128/399 |
| 4,318,722 | 3/1982 | Altman ......................................... 62/3 |
| 4,427,009 | 1/1984 | Wells et al. . |
| 4,445,500 | 5/1984 | Osterholm ................................... 128/1 |
| 4,483,341 | 11/1984 | Witteles ................................... 128/402 |
| 4,502,286 | 3/1985 | Okada et al. ............................. 62/119 |
| 4,569,355 | 2/1986 | Bitterly ................................... 128/691 |

(List continued on next page.)

FOREIGN PATENT DOCUMENTS

| | | |
|---|---|---|
| 0 655 225 A1 | 5/1993 | European Pat. Off. . |
| 0 664 990 | 11/1997 | European Pat. Off. . |
| 2 447 406 | 3/1980 | France . |
| 806 029 | 5/1978 | U.S.S.R. . |
| WO 91/05528 | 5/1991 | WIPO . |
| WO 93/04727 | 3/1993 | WIPO . |
| WO 95/01814 | 1/1995 | WIPO . |
| WO 96/40347 | 12/1996 | WIPO . |
| WO 97/01374 | 1/1997 | WIPO . |
| WO 97/25011 | 7/1997 | WIPO . |
| WO 98/26831 | 6/1998 | WIPO . |
| WO 98/31312 | 7/1998 | WIPO . |

OTHER PUBLICATIONS

Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.

(List continued on next page.)

*Primary Examiner*—Linda C. M. Dvorak
*Assistant Examiner*—R. Kearney
*Attorney, Agent, or Firm*—Gerald W. Spinkle

[57] ABSTRACT

A method for performing hypothermia of a selected organ without significant effect on surrounding organs or other tissues. A flexible coaxial catheter is inserted through the vascular system of a patient to place the distal tip of the catheter in an artery feeding the selected organ. A chilled perfluorocarbon fluid is pumped through an insulated inner supply conduit of the catheter to cool a flexible bellows shaped heat transfer element in the distal tip of the catheter. The heat transfer bellows cools the blood flowing through the artery, to cool the selected organ, distal to the tip of the catheter.

8 Claims, 4 Drawing Sheets

U.S. PATENT DOCUMENTS

| | | | |
|---|---|---|---|
| 4,581,017 | 4/1986 | Sahota | 604/101 |
| 4,655,746 | 4/1987 | Daniels et al. | 604/53 |
| 4,672,962 | 6/1987 | Hershenson | 128/303.1 |
| 4,748,979 | 6/1988 | Hershenson | 128/303.1 |
| 4,750,493 | 6/1988 | Brader | 128/380 |
| 4,762,130 | 8/1988 | Fogarty et al. | 128/348.1 |
| 4,860,744 | 8/1989 | Johnson et al. | 128/303.1 |
| 4,883,455 | 11/1989 | Leonard | 604/4 |
| 4,894,164 | 1/1990 | Polaschegg | 210/646 |
| 4,904,237 | 2/1990 | Janese | 604/28 |
| 4,920,963 | 5/1990 | Brader | 128/402 |
| 4,964,409 | 10/1990 | Tremulis | 128/657 |
| 5,014,695 | 5/1991 | Benak et al. | 128/400 |
| 5,018,521 | 5/1991 | Campbell | 128/363 |
| 5,019,075 | 5/1991 | Spears et al. | 606/7 |
| 5,041,089 | 8/1991 | Mueller et al. | 604/96 |
| 5,078,713 | 1/1992 | Varney | 606/23 |
| 5,092,841 | 3/1992 | Spears | 604/96 |
| 5,106,360 | 4/1992 | Ishwara et al. | 600/2 |
| 5,108,390 | 4/1992 | Potocky et al. | 606/21 |
| 5,110,721 | 5/1992 | Anaise et al. | 435/1 |
| 5,117,822 | 6/1992 | Laghi | 128/400 |
| 5,147,355 | 9/1992 | Friedman et al. | 606/23 |
| 5,149,321 | 9/1992 | Klatz et al. | 604/52 |
| 5,150,706 | 9/1992 | Cox et al. | 128/400 |
| 5,151,100 | 9/1992 | Abele et al. | 606/28 |
| 5,190,539 | 3/1993 | Fletcher et al. | 606/25 |
| 5,191,883 | 3/1993 | Lennox et al. | 128/401 |
| 5,196,024 | 3/1993 | Barath | 606/159 |
| 5,211,631 | 5/1993 | Sheaff | 604/113 |
| 5,234,405 | 8/1993 | Klatz et al. | 604/24 |
| 5,248,312 | 9/1993 | Langberg | 606/28 |
| 5,250,070 | 10/1993 | Parodi | 606/194 |
| 5,257,977 | 11/1993 | Esbel | 404/113 |
| 5,264,260 | 11/1993 | Saab | 428/35.5 |
| 5,269,369 | 12/1993 | Faghri | 607/104 |
| 5,269,749 | 12/1993 | Koturov | 604/4 |
| 5,269,758 | 12/1993 | Taheri | 604/96 |
| 5,281,213 | 1/1994 | Milder et al. | 606/15 |
| 5,281,215 | 1/1994 | Milder | 606/20 |
| 5,310,440 | 5/1994 | Zingher | 156/345 |
| 5,334,193 | 8/1994 | Nardella | 606/41 |
| 5,342,301 | 8/1994 | Saab | 604/96 |
| 5,344,436 | 9/1994 | Fontenot et al. | 607/104 |
| 5,365,750 | 11/1994 | Greenthal | 62/293 |
| 5,368,591 | 11/1994 | Lennox et al. | 606/27 |
| 5,383,918 | 1/1995 | Panetta | 607/104 |
| 5,395,314 | 3/1995 | Klatz et al. | 604/24 |
| 5,395,331 | 3/1995 | O'Neill et al. | 604/96 |
| 5,403,281 | 4/1995 | O'Neill et al. | 604/113 |
| 5,417,686 | 5/1995 | Peterson et al. | 606/25 |
| 5,423,745 | 6/1995 | Todd et al. | 604/53 |
| 5,423,807 | 6/1995 | Milder | 606/20 |
| 5,433,740 | 7/1995 | Yamaguchi | 607/102 |
| 5,437,673 | 8/1995 | Baust et al. | 606/23 |
| 5,452,582 | 9/1995 | Longsworth | 62/51.2 |
| 5,462,521 | 10/1995 | Brucker et al. | 604/20 |
| 5,486,204 | 1/1996 | Clifton | 607/96 |
| 5,486,208 | 1/1996 | Ginsburg | 607/106 |
| 5,531,776 | 7/1996 | Ward et al. | 607/105 |
| 5,558,644 | 9/1996 | Boyd et al. | 604/96 |
| 5,573,532 | 11/1996 | Chang et al. | 606/26 |
| 5,584,804 | 12/1996 | Klatz et al. | 604/24 |
| 5,588,438 | 12/1996 | McKown et al. | 128/692 |
| 5,591,162 | 1/1997 | Fletcher et al. | 606/25 |
| 5,620,480 | 4/1997 | Rudie | 607/101 |
| 5,624,392 | 4/1997 | Saab | 604/43 |
| 5,647,051 | 7/1997 | Neer | 388/811 |
| 5,713,941 | 2/1998 | Robins et al. | 607/96 |
| 5,716,386 | 2/1998 | Ward et al. | 607/106 |
| 5,735,809 | 4/1998 | Gorsuch | 604/4 |
| 5,797,878 | 8/1998 | Bleam | 604/196 |
| 5,800,480 | 9/1998 | Augustine et al. | 607/96 |
| 5,807,391 | 9/1998 | Wijkamp | 606/23 |
| 5,824,030 | 10/1998 | Yang et al. | 607/122 |
| 5,827,222 | 10/1998 | Klatz et al. | 604/52 |
| 5,827,237 | 10/1998 | Macoviak et al. | 604/246 |
| 5,833,671 | 11/1998 | Macoviak et al. | 604/247 |
| 5,837,003 | 11/1998 | Ginsburg | 607/106 |
| 5,871,526 | 2/1999 | Gibbs et al. | 606/104 |
| 5,873,835 | 2/1999 | Hastings et al. | 600/488 |
| 5,879,329 | 3/1999 | Ginsburg | 604/93 |
| 5,899,899 | 5/1999 | Arless et al. | 606/22 |
| 5,902,268 | 5/1999 | Saab | 604/96 |
| 5,913,885 | 6/1999 | Klatz et al. | 607/104 |
| 5,913,886 | 6/1999 | Soloman | 607/108 |
| 5,916,242 | 6/1999 | Schwartz | 607/113 |
| 5,957,963 | 9/1999 | Dobak, III | 607/104 |
| 5,989,238 | 11/1999 | Ginsburg | 604/500 |
| 6,019,783 | 2/2000 | Philips et al. | 607/105 |

OTHER PUBLICATIONS

Bigelo; *Hypothermia, Its Possible Role in Cardiac Surgery*; Nov. 1959; pp. 849–866; Annals of Surgery, vol. 132, No. 5.

Cheatle, T.R. et al. (1993); *Cryostripping the long and short saphenous veins*; Br. J. Surg. 80:1283.

Dexter; *Blood Warms as It Blows Retrograde from a Femoral Cannulation Site to the Carotid Artery During Cardiopulmonary Bypass*; Nov. 1994; pp. 393–397; Perfusion, vol. 9, No. 6.

Gillinov; *Superior Cerebral Protection with Profound Hypothermia During Circulatory Arrest*; Nov. 1992; pp. 1432–1439; Ann. Thorac. Surg., vol. 55.

Higazi; *The Effect of Ultrasonic Irradiation and Temperature on Fibrinolytic Activity in Vitro*; Aug. 1992; pp. 251–253; Thrombosis Research, vol. 69, No. 2.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

Kimoto; *Open Heart Surgery under Direct Vision with the Aid of Brain–Cooling by Irrigation*; Jul. 1955; pp. 592–603; Surgery, vol. 39, No. 4.

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stroke Model*; Feb. 1994; pp. 131–138; Brain Research, vol. 647.

Milleret, Rene; *La cryo–chirurgie danes les varices des mimbres inferieurs*; Angiologie; Supplement au No. 110.

Milleret; Abstract of *Cryosclerosis of the Saphenous Veins in Varicose Reflux in the Obese and Elderly*; Oct. 1981; one page; Phlebologie, vol. 34, No. 4.

Parkins; *Brain Cooling in the Prevention of Brain Damage During Periods of Circulatory Occlusion in Dogs*; Apr. 1954; pp. 284–289; Annals of Surgery, vol. 140, No. 3.

Piepgras; *Rapid Active Internal Core Cooling for Induction of Moderate Hypothermia in Head Injury by Use of an Extracorporeal Heat Exchanger*; Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Schwartz; *Cerebral Blood Flow During Low–flow Hypothermic Cardiopulmonary Bypass in Baboons*; Jun. 1994; pp. 959–964; Anesthesiology, vol. 81, No. 4.

Schwartz; *Selective Cerebral Hypothemia by Means of Transfemoral Internal Carotid Artery Catheterization*; May 1996; pp. 571–572; Radiology, vol. 201, No. 2.

Steen; *The Detrimental Effects of Prolonged Hypothermia and Rewarming in the Dog*; Aug. 1979 ;pp. 224–230; Anesthesiology, vol. 52, No. 3.

Vandam; *Hypothermia*; Sep. 1959; pp. 546–553; The New England Journal of Medicine.

White; *Cerebral Hypothermia and Circulatory Arrest*; Jul. 1978; pp. 450–458; Mayo Clinic Proceedings, vol. 53.

Yenari; *Thrombolysis with Tissue Plasminogen Activator (tPA) in Temerature Dependent*; Jul. 1994; pp. 475–481; Thrombosis Research, vol. 77, No. 5.

Yoshihara; *Changes in Coagulation and Fibrinolysis Occurring in Dogs During Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, N. 2.

Marekovic, Z.; Abstract of *Renal Hypothermia in Situ by Venous Passages; Experimental Work on Dogs*; European Urology 6(2), pp. 119–123; 1980.

Schwartz, A.; *Isolated Cerebral Hypothermia by Single Carotid Artery Perfusion of Extracorporeally Cooled Blood in Baboons*; Neurosurgery, vol. 39, No. 3, pp. 577–582; Sep., 1996.

Jansen, J.; *Near Continuous Cardiac Output by Thermodilution*; Journal of Clinical Monitoring, vol. 13; Jun. 26, 1996; pp. 233–239.

CIRCULATING FLUID HYPOTHERMIA METHOD

CROSS REFERENCE TO RELATED APPLICATIONS

This application is a divisional application of pending U.S. Ser. No. 09/052,545, filed Mar. 31, 1998, titled "Circulating Fluid Hypothermia Method And Apparatus".

STATEMENT REGARDING FEDERALLY SPONSORED RESEARCH OR DEVELOPMENT

Not Applicable

BACKGROUND OF THE INVENTION

1. Field of the Invention

The current invention relates to selective cooling, or hypothermia, of an organ, such as the brain, by cooling the blood flowing into the organ. This cooling can protect the tissue from injury caused by anoxia or trauma.

2. Background Information

Organs of the human body, such as the brain, kidney, and heart, are maintained at a constant temperature of approximately 37° C. Cooling of organs below 35° C. is known to provide cellular protection from anoxic damage caused by a disruption of blood supply, or by trauma. Cooling can also reduce swelling associated with these injuries.

Hypothermia is currently utilized in medicine and is sometimes performed to protect the brain from injury. Cooling of the brain is generally accomplished through whole body cooling to create a condition of total body hypothermia in the range of 20° to 30° C. This cooling is accomplished by immersing the patient in ice, by using cooling blankets, or by cooling the blood flowing externally through a cardiopulmonary bypass machine. U.S. Pat. No. 3,425,419 to Dato and U.S. Pat. No. 5,486,208 to Ginsburg disclose catheters for cooling the blood to create total body hypothermia.

Total body hypothermia to provide organ protection has a number of drawbacks. First, it creates cardiovascular problems, such as cardiac arrhythmias, reduced cardiac output, and increased systemic vascular resistance. These side effects can result in organ damage. These side effects are believed to be caused reflexively in response to the reduction in core body temperature. Second, total body hypothermia is difficult to administer. Immersing a patient in ice water clearly has its associated problems. Placement on cardiopulmonary bypass requires surgical intervention and specialists to operate the machine, and it is associated with a number of complications including bleeding and volume overload. Third, the time required to reduce the body temperature and the organ temperature is prolonged. Minimizing the time between injury and the onset of cooling has been shown to produce better clinical outcomes.

Some physicians have immersed the patient's head in ice to provide brain cooling. There are also cooling helmets, or head gear, to perform the same. This approach suffers from the problems of slow cool down and poor temperature control due to the temperature gradient that must be established externally to internally. It has also been shown that complications associated with total body cooling, such as arrhythmia and decreased cardiac output, can also be caused by cooling of the face and head only.

Selective organ hypothermia has been studied by Schwartz, et. al. Utilizing baboons, blood was circulated and cooled externally from the body via the femoral artery and returned to the body through the carotid artery. This study showed that the brain could be selectively cooled to temperatures of 20° C. without reducing the temperature of the entire body. Subsequently, cardiovascular complications associated with total body hypothermia did not occur. However, external circulation of the blood for cooling has not yet been a widely accepted approach for the treatment of humans. The risks of infection, bleeding, and fluid imbalance are great. Also, at least two arterial vessels must be punctured and cannulated. Further, percutaneous cannulation of the carotid artery is very difficult and potentially fatal, due to the associated arterial wall trauma. Also, this method could not be used to cool organs such as the kidneys, where the renal arteries cannot be directly cannulated percutaneously.

Selective organ hypothermia has also been attempted by perfusing the organ with a cold solution, such as saline or perflourocarbons. This is commonly done to protect the heart during heart surgery and is referred to as cardioplegia. This procedure has a number of drawbacks, including limited time of administration due to excessive volume accumulation, cost and inconvenience of maintaining the perfusate, and lack of effectiveness due to temperature dilution from the blood. Temperature dilution by the blood is a particular problem in high blood flow organs such as the brain. For cardioplegia, the blood flow to the heart is minimized, and therefore this effect is minimized.

Intravascular, selective organ hypothermia, created by cooling the blood flowing into the organ, is the ideal method. First, because only the target organ is cooled, complications associated with total body hypothermia are avoided. Second, because the blood is cooled intravascularly, or in situ, problems associated with external circulation of blood are eliminated. Third, only a single puncture and arterial vessel cannulation is required, and it can be performed at an easily accessible artery such as the femoral, subclavian, or brachial. Fourth, cold perfusate solutions are not required, thus eliminating problems with excessive fluid accumulation. This also eliminates the time, cost, and handling issues associated with providing and maintaining cold perfusate solution. Fifth, rapid cooling can be achieved. Sixth, precise temperature control is possible.

Previous inventors have disclosed the circulation of cold water or saline solution through an uninsulated catheter in a major vessel of the body to produce total body hypothermia. This approach has not been successful at selective organ hypothermia, for reasons demonstrated below.

The important factor related to catheter development for selective organ hypothermia is the small size of the typical feeding artery, and the need to prevent a significant reduction in blood flow when the catheter is placed in the artery. A significant reduction in blood flow would result in ischemic organ damage. While the diameter of the major vessels of the body, such as the vena cava and aorta, are as large as 15 to 20 mm., the diameter of the feeding artery of an organ is typically only 4.0 to 8.0 mm. Thus, a catheter residing in one of these arteries cannot be much larger than 2.0 to 3.0 mm. in outside diameter. It is not practical to construct a selective organ hypothermia catheter of this small size using the circulation of cold water or saline solution. Using the brain as an example, this point will be illustrated.

The brain typically has a blood flow rate of approximately 500 to 750 cc/min. Two carotid arteries feed this blood supply to the brain. The internal carotid is a small diameter artery that branches off of the common carotid near the angle of the jaw. To cool the brain, it is important to place some of the cooling portion of the catheter into the internal carotid artery, so as to minimize cooling of the face via the external carotid, since face cooling can result in complications, as discussed above. It would be desirable to cool the blood in this artery down to 32° C., to achieve the desired cooling of the brain. To cool the blood in this artery by a 5°°C. drop, from 37° C. down to 32° C., requires between 100 and 150 watts of refrigeration power.

In order to reach the internal carotid artery from a femoral insertion point, an overall catheter length of approximately 100 cm. would be required. To avoid undue blockage of the blood flow, the outside diameter of the catheter can not exceed approximately 2 mm. Assuming a coaxial construction, this limitation in diameter would dictate an internal supply tube of about 0.70 mm. diameter, with return flow being between the internal tube and the external tube.

A catheter based on the circulation of fluid operates on the principle of transferring heat from the blood to raise the temperature of the water. The fluid must warm up to absorb heat and produce cooling. Water flowing at the rate of 5.0 grams/sec, at an initial temperature of 0° C. and warming up to 5° C., can absorb 100 watts of heat. Thus, the outer surface of the heat transfer element could only be maintained at 5° C., instead of 0° C. This will require the heat transfer element to have a surface area of approximately 1225 mm$^2$. If a catheter of approximately 2.0 mm. diameter is assumed, the length of the heat transfer element would have to be approximately 20 cm.

In actuality, if circulated through an uninsulated catheter, the water or saline solution would undoubtedly warm up before it reached the heat transfer element, and provision of 0° C. water at the heat transfer element would be impossible. Circulating a cold liquid through an uninsulated catheter also would cause cooling along the catheter body and could result in non-specific or total body hypothermia. Furthermore, to achieve this heat transfer rate, 5 grams/sec of water flow are required. To circulate water through a 100 cm. long, 0.70 mm. diameter supply tube at this rate produces a pressure drop of more than 3000 psi. This pressure exceeds the safety levels of many flexible medical grade plastic catheters. Further, it is doubtful whether a water pump that can generate these pressures and flow rates can be placed in an operating room.

BRIEF SUMMARY OF THE INVENTION

The selective organ cooling achieved by the present invention is accomplished by placing a coaxial cooling catheter into the feeding artery of the organ. Cold perfluorocarbon fluid is circulated through the catheter. In the catheter, a shaft or body section would carry the perfluorocarbon fluid to a distal flexible heat transfer element where cooling would occur. A preferred heat transfer element would be bellows shaped. Cooling of the catheter tip to temperatures above minus 2° C. results in cooling of the blood flowing into the organ located distally of the catheter tip, and subsequent cooling of the target organ. For example, the catheter could be placed into the internal carotid artery, to cool the brain. The size and location of this artery places significant demands on the size and flexibility of the catheter. Specifically, the outside diameter of the catheter must be minimized, so that the catheter can fit into the artery without compromising blood flow. An appropriate catheter for this application would have a flexible body of 70 to 100 cm. in length and 2.0 to 3.0 mm. in outside diameter.

It is important for the catheter to be flexible in order to successfully navigate the arterial path, and this is especially true of the distal end of the catheter. So, the distal end of the catheter must have a flexible heat transfer element, which is composed of a material which conducts heat better than the remainder of the catheter. The catheter body material could be nylon or PBAX, and the heat transfer element could be made from a material having higher thermal conductivity, such as nitinol, nickel, copper, silver, or gold. Ideally, the heat transfer element is formed with a maximized or convoluted surface area, such as a bellows. A bellows has a convoluted surface, with fin-like annular folds, causing the bellows to be very flexible, even though the bellows is constructed of a metallic material. Further, the convoluted surface of the bellows causes it to have a much larger surface area than a straight tube of the same length. Still further, the bellows is axially compressible, making it ideal for use on the tip of a catheter which will be navigated through the vascular system of a patient. If the bellows abuts the wall of an artery, the bellows will easily compress, thereby eliminating or reducing the trauma to the arterial wall.

Bellows can be formed with known techniques to be seamless and non-porous, therefore being impermeable to gas. Metallic bellows in the sizes appropriate for use in the present invention are known, which have helium leak rates less than $10^{-6}$ cc/sec. Impermeability and low leakage are particularly important for use in the present invention, where refrigerant gas will be circulated through the vascular system of a patient.

Bellows are also mechanically robust, being capable of withstanding more than 10,000 cycles of axial loading and unloading. Further, metallic bellows are known to tolerate the cryogenic temperatures generated in the device of the present invention, without loss of performance. Finally, metallic bellows can be made in large quantities, relatively inexpensively, making them ideal for use in disposable medical device.

Because the catheter body and heat transfer element of the present invention may dwell in the vascular system of the patient for extended periods, up to 48 hours in some cases, they might be susceptible to blood clot formation if no preventive measures are taken. This is particularly true of the bellows design, because some blood stasis may occur in the annular folds of the bellows, allowing clot forming agents to cling to the bellows surface and form a thrombus. Therefore, treatment of the catheter body and bellows surfaces to prevent clot formation is desirable. One such treatment is the binding of antithrombogenic agents, such as heparin, to the surface. Another such treatment is the bombardment of the surface with ions, such as nitrogen ions, to harden and smooth the surface, thereby preventing clot forming agents from clinging to the surface.

The heat transfer element would require sufficient surface area to absorb 100 to 150 watts of heat, in the carotid artery example. This could be accomplished with a bellows element of approximately 2 mm. diameter, 13 cm. in length, with a surface temperature of 0° C. The cooling would be provided by the circulation of a perfluorocarbon fluid through an inner supply tube, returning through the annular space between the inner supply tube and the outer tubular catheter body. The inner tube has insulating means, such as longitudinal channels. The longitudinal channels can be filled with a gas, or evacuated. Further, the outer tube of the catheter body can have insulating means, such as longitudinal channels, which also can be filled with a gas or evacuated.

For example, a perfluorocarbon fluid flowing at a flow rate of between two (2) and three (3) grams/sec could provide between approximately 100 and 150 watts of refrigeration power. Utilizing an insulated catheter allows the cooling to be focused at the heat transfer element, thereby eliminating cooling along the catheter body. Utilizing perfluorocarbon fluid also lowers the fluid flow rate requirement, as compared to water or saline solution, to remove the necessary amount of heat from the blood. This is important because the required small diameter of the catheter would have higher pressure drops at higher flow rates.

The catheter would be built in a coaxial construction with a 1.25 mm. inner supply tube diameter and a 2.5 mm. outer return tube diameter. This results in tolerable pressure drops of the fluid along the catheter length, as well as minimizing the catheter size to facilitate carotid placement. The inner tube would carry the perfluorocarbon fluid to the heat transfer bellows element at the distal end of the catheter body. If a bellows surface temperature of 0° C. is maintained, just above the freezing point of blood, then 940 $mm^2$ of surface area in contact with the blood are required to lower the temperature of the blood by the specified 5° C. drop. This translates to a 2.0 mm. diameter heat transfer bellows by 13 cm. in length. To generate 0° C. on the bellows surface, the perfluorocarbon fluid must be supplied at a temperature of minus 50° C.

It is important to use a perfluorocarbon fluid, for several reasons. First, these compounds have very low viscosities, even at low temperatures. Therefore, they can be circulated through small tubing at high flow rates, with much less pressure drop than water or saline solution. Second, they can be cooled below 0° C. without freezing, allowing colder fluid to be delivered to the heat transfer element. Since more heat can be transferred to the lower temperature heat transfer element, lower flow rates are required to achieve the same cooling capacity as higher flow rates of water or saline. This further decreases the pressure drop experienced in the tubing. Since some warming is likely to occur along the catheter body, it is also helpful to use a fluid which can be cooled to a lower temperature, thereby delivering the desired cooling capacity at the distal tip of the catheter.

Third, perfluorocarbon fluids have very low surface tension, as compared to water or saline solution. This is important in applications where the heat transfer element has highly convoluted surface contours to maximize surface area, such as the bellows heat transfer element. A fluid with low surface tension will wet the internal surface of such a heat transfer element, resulting in increased heat transfer, whereas a fluid with a higher surface tension, such as water, which will not completely wet the surface. Fourth, perfluorocarbon fluids are inert and non-toxic compounds, even having been used as blood substitutes. This is an important safety concern, in the event of a leak. Finally, perfluorocarbon fluids are chemically compatible with many of the plastics which are used in making catheters. This is important, since catheter deterioration could be a serious problem in applications where the catheter may remain in the vascular system of the patient, circulating fluid, for long periods of time.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
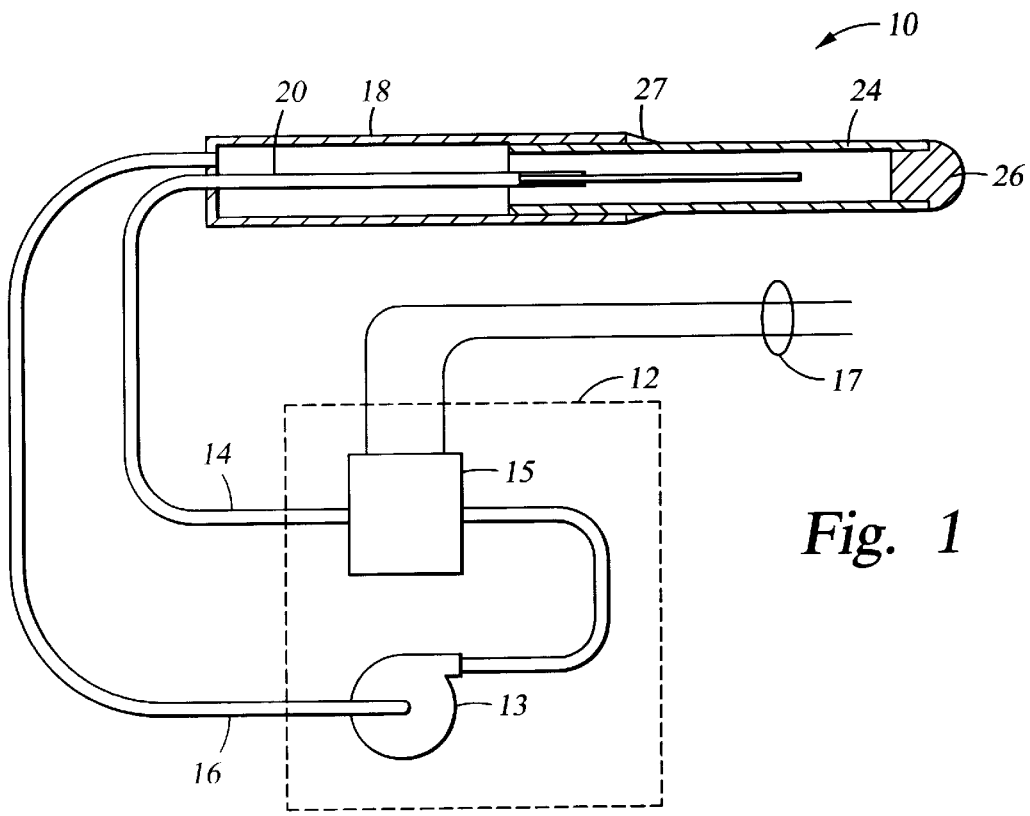
FIG. 1 is a schematic, partially in section, of the apparatus of the present invention, showing a first embodiment of the flexible catheter.

As shown in FIG. 1, the apparatus includes a flexible coaxial catheter assembly 10, fed by a pumping or circulating unit 12, which can include a pump 13 and a chiller 15, with a freon based refrigerant loop 17. The circulating unit 12 has an outlet 14 and an inlet 16. The catheter assembly 10 has an outer flexible catheter body 18, which can be made of braided PBAX or other suitable catheter material. The catheter assembly 10 also has an inner flexible perfluorocarbon supply conduit 20, which can be made of nylon, polyimide, PBAX, or other suitable catheter material. Both the catheter body 18 and the supply conduit 20 should be insulated, with a preferred means of insulation being discussed in more detail below.

The lumen 19 of the catheter body 18 serves as the return flow path for the circulating perfluorocarbon. The catheter body 18 and the supply conduit 20 must be flexible, to enable passage through the vascular system of the patient to the feeding artery of the selected organ. The length and diameter of the catheter body 18 and perfluorocarbon supply conduit 20 are designed for the size and location of the artery in which the apparatus will be used. For use in the internal carotid artery to achieve hypothermia of the brain, the catheter body 18 and perfluorocarbon supply conduit 20 will have a length of approximately 70 to 100 centimeters. The catheter body 18 for this application will have an outside diameter of approximately 2.5 millimeters and an inside diameter of approximately 2.0 millimeters, and the perfluorocarbon supply conduit 20 will have an outside diameter of approximately 1.25 millimeter and an inside diameter of approximately 1.0 millimeter. A supply conduit 20 and a return flow path through a catheter body 18 of these diameters will have a perfluorocarbon pressure drop of significantly less than the pressure drop that would be exhibited by water or a saline solution.

The circulating unit outlet 14 is attached in fluid flow communication, by known means, to a proximal end of the perfluorocarbon supply conduit 20 disposed coaxially within said catheter body 18. The distal end of the perfluorocarbon supply conduit 20 has an outlet adjacent to or within a chamber of a flexible heat transfer element such as the hollow flexible tube 24. The tube 24 shown in this embodiment is flexible but essentially straight in its unflexed state. The heat transfer element must be flexible, to enable passage through the vascular system of the patient to the feeding artery of the selected organ. For the internal carotid application the flexible tube 24 will have a length of approximately 15 centimeters, an outside diameter of approximately 1.9 millimeters and an inside diameter of approximately 1.5 millimeters. The heat transfer element also includes a plug 26 in the distal end of the flexible tube 24. The plug 26 can be epoxy potting material, plastic, or a metal such as stainless steel or gold. A tapered transition of epoxy potting material can be provided between the catheter body 18 and the flexible tube 24.

A perfluorocarbon, such as FC-77, made by Dupont, is chilled and pumped through the perfluorocarbon supply conduit 20 into the interior chamber of the heat transfer element, such as the flexible tube 24, thereby cooling the heat transfer element 24. Blood in the feeding artery flows around the heat transfer element 24, thereby being cooled. The blood then continues to flow distally into the selected organ, thereby cooling the organ. FC-77 is a suitable perfluorocarbon, because it has a freezing point of −110° C., a viscosity of 0.8 centistokes at 25° C., and a surface tension of 15 dynes per centimeter. Other suitable perfluorocarbons include FC-72 and FC-75, also made by Dupont.

Figure 2:
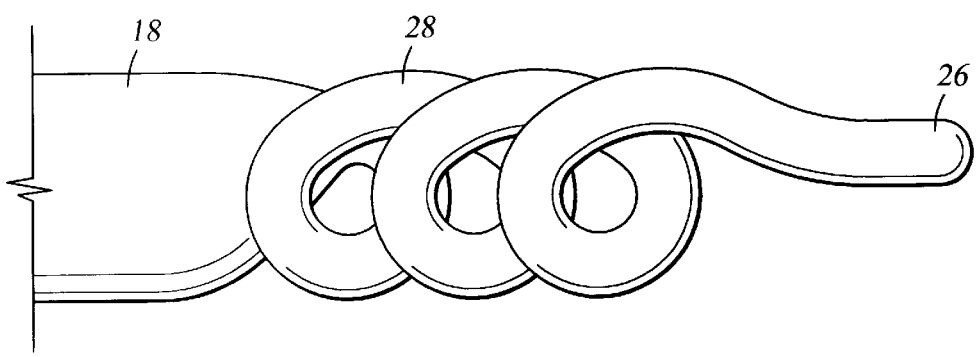
FIG. 2 is a perspective view of a second embodiment of the distal tip of the catheter.

A second embodiment of the heat transfer element is shown in FIG. 2. This embodiment can be constructed of a tubular material such as nitinol, which has a temperature dependent shape memory. The heat transfer element 28 can be originally shaped like the flexible tube 24 shown in FIG. 1, at room temperature, but trained to take on the coiled tubular shape shown in FIG. 2 at a lower temperature. This allows easier insertion of the catheter assembly 10 through the vascular system of the patient, with the essentially straight but flexible tubular shape, similar to the flexible tube 24. Then, when the heat transfer element is at the desired location in the feeding artery, such as the internal carotid artery, circulation of chilled perfluorocarbon is commenced. As the chilled perfluorocarbon cools the heat transfer element down, the heat transfer element takes on the shape of the heat transfer coil 28 shown in FIG. 2. This enhances the heat transfer capacity, while limiting the length of the heat transfer element.

Figure 3:
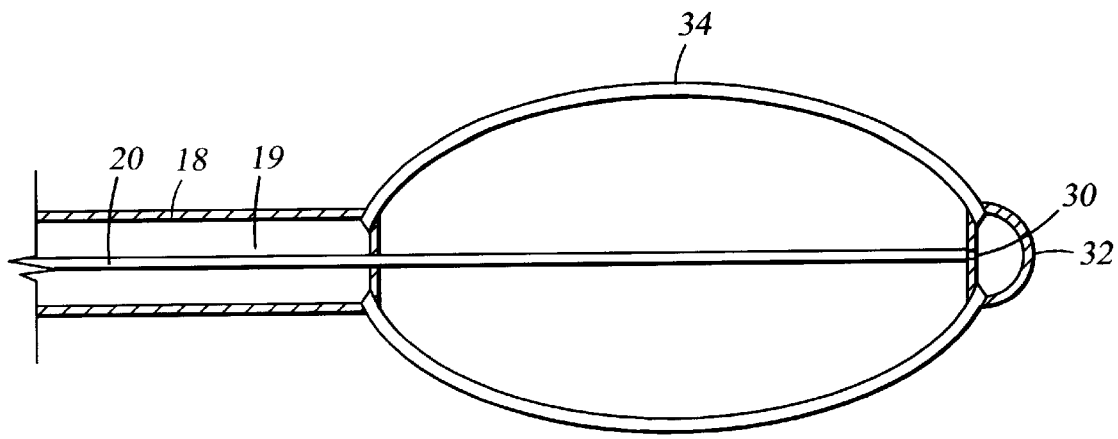
FIG. 3 is a section view of a third embodiment of the distal tip of the catheter.

A third embodiment of the heat transfer element is shown in FIG. 3. In this embodiment, the perfluorocarbon supply conduit 20 has an outlet 30 in an interior chamber 32 at the distal end of the heat transfer element. The heat transfer element is a plurality of hollow tubes 34 leading from the interior chamber 32 of the heat transfer element to the perfluorocarbon return lumen 19 of the catheter body 18. This embodiment of the heat transfer element 34 can be constructed of a tubular material such as nitinol, which has a temperature dependent shape memory, or some other tubular material having a permanent bias toward a curved shape. The heat transfer element tubes 34 can be essentially straight, originally, at room temperature, but trained to take on the outwardly flexed "basket" shape shown in FIG. 3 at a lower temperature. This allows easier insertion of the catheter assembly 10 through the vascular system of the patient, with the essentially straight but flexible tubes. Then, when the heat transfer element 34 is at the desired location in the feeding artery, such as the internal carotid artery, refrigerant flow is commenced. As the expanding refrigerant cools the heat transfer element 34 down, the heat transfer element takes on the basket shape shown in FIG. 3. This enhances the heat transfer capacity, while limiting the length of the heat transfer element.

Figure 4:
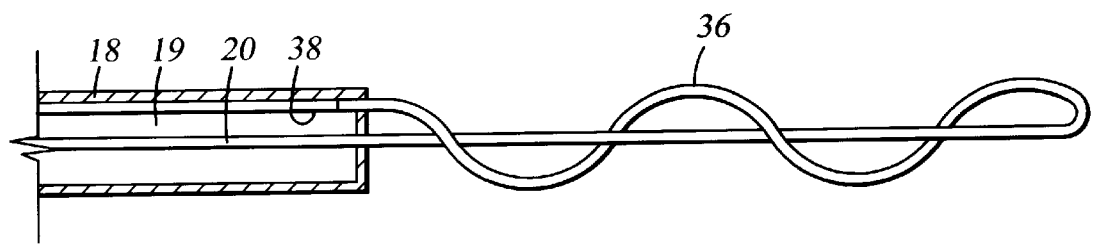
FIG. 4 is a partial section view of a fourth embodiment of the distal tip of the catheter.

A fourth embodiment of the heat transfer element is shown in FIG. 4. This embodiment can be constructed of a material such as nitinol. The heat transfer element 36 can be originally shaped as a long loop connecting the distal end of the catheter body 18 to the distal end of the perfluorocarbon supply conduit 20, at room temperature, but trained to take on the coiled tubular shape shown in FIG. 4 at a lower temperature, with the heat transfer element 36 coiled around the perfluorocarbon supply conduit 20. This allows easier insertion of the catheter assembly 10 through the vascular system of the patient, with the essentially straight but flexible tubular loop shape. Then, when the heat transfer element 36 is at the desired location in the feeding artery, such as the internal carotid artery, circulation of chilled perfluorocarbon is commenced. As the chilled perfluorocarbon cools the heat transfer element 36 down, the heat transfer element 36 takes on the shape of the coil shown in FIG. 4. The convoluted surface of this coil enhances the heat transfer capacity, while limiting the length of the heat transfer element 36. FIG. 4 further illustrates that a thermocouple 38 can be incorporated into the catheter body 18 for temperature sensing purposes.

Figure 5:
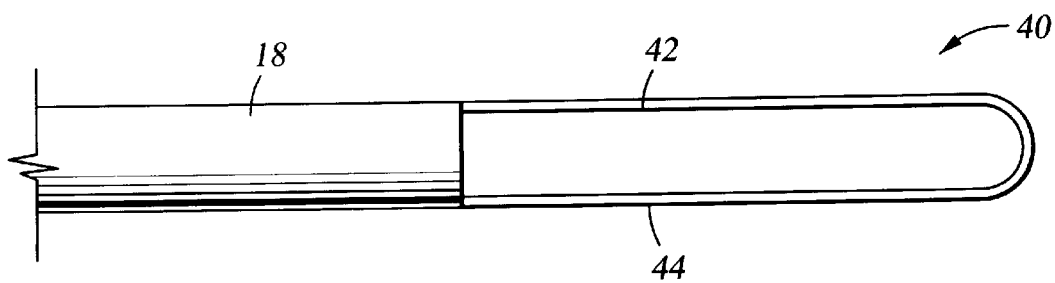
FIG. 5 is an elevation view of a fifth embodiment of the distal tip of the catheter.
Figure 6:
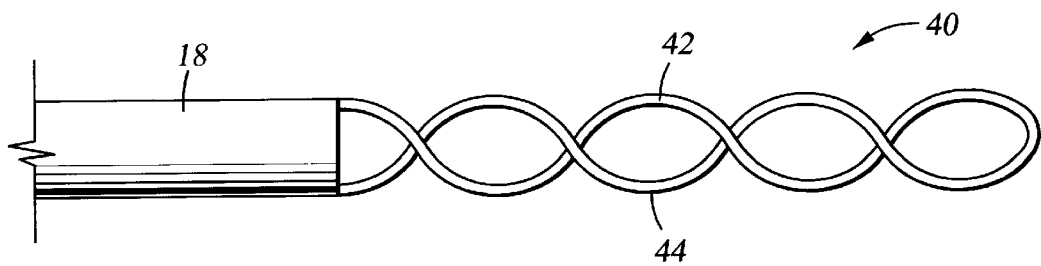
FIG. 6 is an elevation view of the embodiment shown in FIG. 5, after transformation to a double helix.
Figure 7:
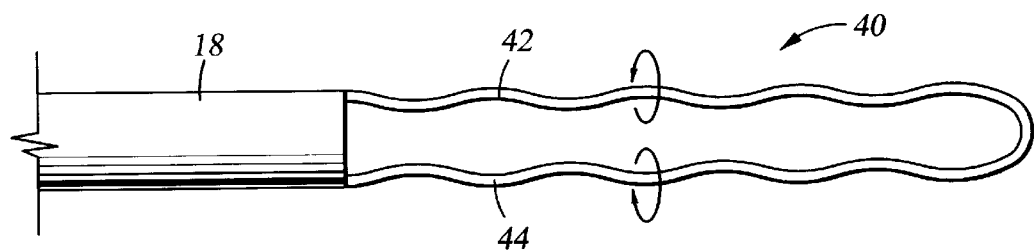
FIG. 7 is an elevation view of the embodiment shown in FIG. 5, after transformation to a looped coil.

Yet a fifth embodiment of the heat transfer element is shown in FIGS. 5, 6, and 7. This embodiment of the heat transfer element can be constructed of a material such as nitinol. The heat transfer element is originally shaped as a long loop 40 extending from the distal ends of the catheter body 18 and the perfluorocarbon supply conduit 20, at room temperature. The long loop 40 has two sides 42, 44, which are substantially straight but flexible at room temperature. The sides 42, 44 of the long loop 40 can be trained to take on the double helical shape shown in FIG. 6 at a lower temperature, with the two sides 42, 44 of the heat transfer element 40 coiled around each other. Alternatively, the sides 42, 44 of the long loop 40 can be trained to take on the looped coil shape shown in FIG. 7 at a lower temperature, with each of the two sides 42, 44 of the heat transfer element 40 coiled independently. Either of these shapes allows easy insertion of the catheter assembly 10 through the vascular system of the patient, with the essentially straight but flexible tubular loop shape. Then, when the heat transfer element 40 is at the desired location in the feeding artery, such as the internal carotid artery, circulation of chilled perfluorocarbon is commenced. As the chilled perfluorocarbon cools the heat transfer element 40 down, the heat transfer element 40 takes on the double helical shape shown in FIG. 6 or the looped coil shape shown in FIG. 7. Both of these configurations give the heat transfer element 40 a convoluted surface, thereby enhancing the heat transfer capacity, while limiting the length of the heat transfer element 40.

Figure 8:
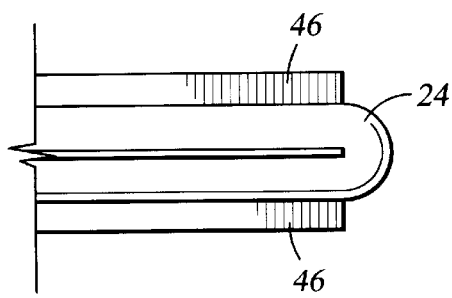
FIG. 8 is an elevation view of a sixth embodiment of the distal tip of the catheter, showing longitudinal fins on the heat transfer element.
Figure 9:
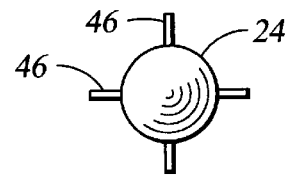
FIG. 9 is an end view of the embodiment shown in FIG. 8.

As shown in FIGS. 8 through 11, the tubular heat transfer element 24 can have external fins 46, 48 attached thereto, such as by welding or brazing, to give the heat transfer element 24 a convoluted surface, thereby promoting heat transfer. Use of a convoluted surface, such as fins, allows the use of a shorter heat transfer element without reducing the heat transfer surface area, or increases the heat transfer surface area for a given length. In FIGS. 8 and 9, a plurality of longitudinal fins 46 are attached to the heat transfer element 24. The heat transfer element 24 in such an embodiment can have a diameter of approximately 1.0 millimeter, while each of the fins 46 can have a width of approximately 0.5 millimeter and a thickness of approximately 0.12 millimeter. This will give the heat transfer element an overall diameter of approximately 2.0 millimeters, still allowing the catheter to be inserted into the internal carotid artery.

Figure 10:
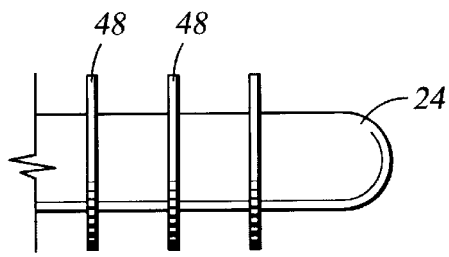
FIG. 10 is an elevation view of a seventh embodiment of the distal tip of the catheter, showing annular fins on the heat transfer element.
Figure 11:
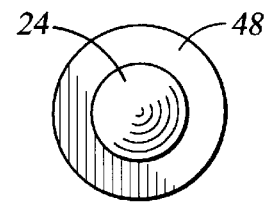
FIG. 11 is an end view of the embodiment shown in FIG. 10.

In FIGS. 10 and 11, a plurality of annular fins 48 are attached to the heat transfer element 24. The heat transfer element 24 in such an embodiment can have a diameter of approximately 1.0 millimeter, while each of the fins 48 can have a width of approximately 0.5 millimeter and a thickness of approximately 0.12 millimeter. This will give the heat transfer element an overall diameter of approximately 2.0 millimeters, still allowing the catheter to be inserted into the internal carotid artery.

Figure 12:
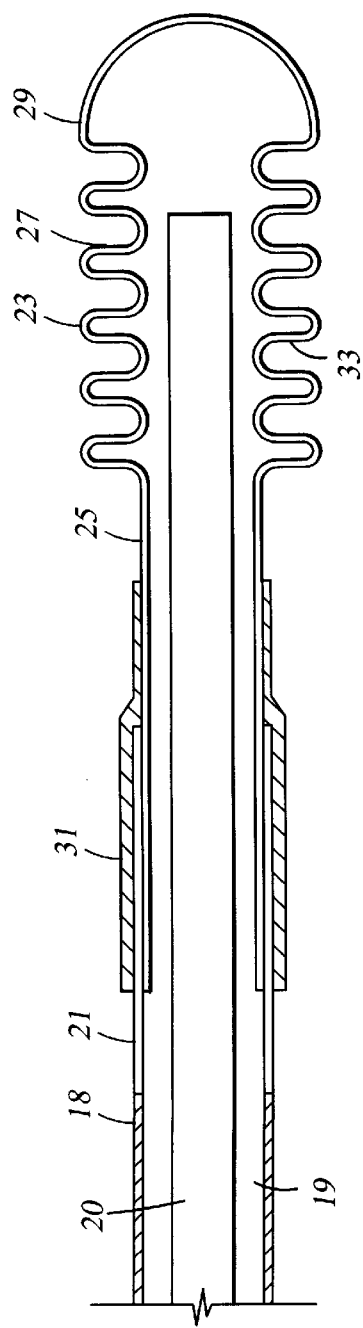
FIG. 12 is a longitudinal section of the distal tip of an eighth embodiment of the catheter of the present invention, showing a bellows heat transfer element.

As shown in FIG. 12, the present invention can include a bellows shaped heat transfer element 23 on the distal end of the catheter body 18. The heat transfer bellows 23 can be constructed of a metal having a high thermal conductivity, such as nitinol, nickel, copper, silver, gold, or some other suitable material. The catheter body 18 of braided PBAX can have a distal section 21 of non-braided PBAX. The heat transfer bellows 23 comprises a tubular throat 25 fitted within the distal section 21 of the catheter. A plurality of annular folds 27 extend from the distal end of the throat 25. An end cap 29 is formed at the distal end of the annular folds 27.

The distal section 21 of non-braided PBAX can be melted or shrunk onto the bellows throat 25. A shrink fit tube 31 of a suitable plastic can be formed onto the distal section 21 of the catheter and the bellows throat 25, to form a smooth transition. To prevent thrombosis, an antithrombogenic agent such as heparin can be bonded to the outer surface 33 of the bellows 23, particularly on the annular folds 27. Alternatively, the outer surface 33 of the bellows 23 can be nitrided or subjected to a similar treatment to create a smooth surface which retards thrombosis.

Figure 13:
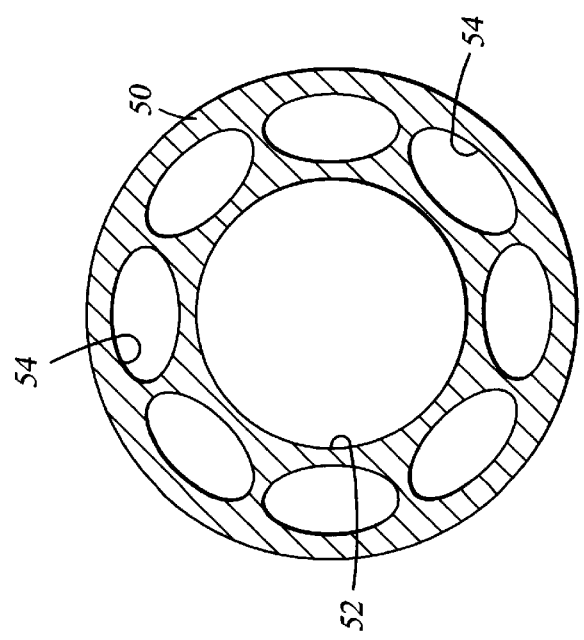
FIG. 13 is a transverse section of one embodiment of an insulated single wall tube for use in the present invention.

The inner perfluorocarbon supply conduit 20 should be insulated to prevent warming of the cold supply perfluorocarbon by the warmer return perfluorocarbon in the outer lumen 19. In one embodiment, a single wall perfluorocarbon supply conduit 20 could be constructed with a ring of parallel longitudinal lumens in the wall of the conduit 20, surrounding the cold perfluorocarbon flow path. These parallel longitudinal lumens could be evacuated, actively or passively, or filled with insulating material. Similarly, the outer lumen 19 of the catheter body 18, which carries the return perfluorocarbon flow, could be insulated, to reduce the warming of the return flow by the blood surrounding the catheter body 18. FIG. 13 is a transverse section of an insulated single wall tube which could be used for either the insulated catheter body 18 or the supply conduit 20, or both. The catheter body 18 or supply conduit 20 has a single wall 50, with an inner lumen 52 for flow of the perfluorocarbon. A plurality of longitudinal insulating lumens 54 are arranged surrounding, and parallel to, the inner lumen 52. Each insulating lumen 54 can be evacuated during manufacture of the circulating catheter assembly 10. If evacuated during manufacture, each of the insulating lumens 54 could be sealed at its proximal end, creating a constant, passive vacuum in each of the insulating lumens 54. Alternatively, the insulating lumens 54 could be evacuated during use of the circulating catheter assembly 10, such as by the use of a vacuum pump or syringe (not shown). Conversely, the insulating lumens 54 could be filled with an insulating material. As mentioned above, this insulated single wall design could be used for the supply conduit 20, or the catheter body 18, or both.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A method for selective organ hypothermia, said method comprising:

providing a circulating fluid apparatus having a chiller and a flexible coaxial catheter, said catheter having an insulated inner lumen and a hollow flexible heat transfer element adjacent its distal tip;

inserting said catheter through the vascular system of a patient to place said heat transfer element in a feeding artery of a selected organ;

supplying chilled perfluorocarbon fluid to said insulated inner lumen of said coaxial catheter;

cooling the interior of said heat transfer element with said chilled perfluorocarbon fluid;

cooling blood flowing in said feeding artery with said heat transfer element, to enable said cooled blood to flow distally into said selected organ and cool said organ; and returning said perfluorocarbon fluid to said chiller.

2. A method for selective organ hypothermia, said method comprising:

providing a coaxial catheter, said catheter having an insulated inner lumen and a metallic heat transfer element;

introducing said coaxial catheter into the vascular system of a patient to place said metallic heat transfer element in a feeding artery of an organ of the patient;

cooling said metallic heat transfer element by circulating a refrigerant through said insulated inner lumen of said coaxial catheter;

cooling blood in said feeding artery by contact with said cooled metallic heat transfer element; and cooling said organ by flow of said cooled blood through said feeding artery.

3. A method for selective brain hypothermia, comprising:

providing a flexible coaxial catheter, said flexible catheter having an insulated inner lumen and a flexible metallic heat transfer element;

introducing said flexible coaxial catheter into the vascular system of a patient to place said flexible metallic heat transfer element in the carotid artery of the patient;

cooling said flexible metallic heat transfer element by circulating a refrigerant through said insulated inner lumen of said flexible coaxial catheter;

cooling blood in said carotid artery by contact with said cooled flexible metallic heat transfer element; and cooling the brain of the patient by flow of said cooled blood through said carotid artery.

4. A method for selective hypothermia of the heart of a patient, comprising:

providing a flexible coaxial catheter, said flexible coaxial catheter having an insulated inner lumen and a flexible metallic heat transfer element;

introducing said flexible coaxial catheter into the vascular system of a patient to place said flexible metallic heat transfer element in a feeding artery of the heart of the patient;

cooling said flexible metallic heat transfer element by circulating a refrigerant through said insulated inner lumen of said flexible coaxial catheter;

cooling blood in said feeding artery by contact with said cooled flexible metallic heat transfer element; and cooling the heart of the patient by flow of said cooled blood through said feeding artery.

5. A method for selective organ hypothermia, said method comprising:

providing a circulating fluid apparatus having a chiller and a flexible coaxial catheter, said catheter having an inner lumen and a hollow flexible heat transfer element adjacent its distal tip;

inserting said catheter through the vascular system of a patient to place said heat transfer element in a feeding artery of a selected organ;

supplying chilled perfluorocarbon fluid to said inner lumen of said coaxial catheter;

cooling the interior of said heat transfer element with said chilled perfluorocarbon fluid;

cooling blood flowing in said feeding artery with said heat transfer element, to enable said cooled blood to flow distally into said selected organ and cool said organ; and returning said perfluorocarbon fluid to said chiller.

6. A method for organ hypothermia, said method comprising:

providing a coaxial catheter, said catheter having an inner lumen and a metallic heat transfer element;

introducing said coaxial catheter into the vascular system of a patient to place said metallic heat transfer element in an artery of an organ of the patient;

cooling said metallic heat transfer element by circulating a refrigerant through said inner lumen of said coaxial catheter;

cooling blood in said artery by contact with said cooled metallic heat transfer element; and cooling said organ by flow of said cooled blood through said artery.

7. A method for selective brain hypothermia, comprising:

providing a flexible coaxial catheter, said flexible catheter having an inner lumen and a flexible heat transfer element;

introducing said flexible coaxial catheter into the vascular system of a patient to place said flexible heat transfer element in the carotid artery of the patient;

cooling said flexible heat transfer element by circulating a refrigerant through said inner lumen of said flexible coaxial catheter;

cooling blood in said carotid artery by contact with said cooled flexible heat transfer element; and cooling the brain of the patient by flow of said cooled blood through said carotid artery.

8. A method for selective hypothermia of the heart of a patient, comprising:

providing a flexible coaxial catheter, said flexible coaxial catheter having an inner lumen and a flexible heat transfer element;

introducing said flexible coaxial catheter into the vascular system of a patient to place said flexible heat transfer element in a feeding artery of the heart of the patient;

cooling said flexible heat transfer element by circulating a refrigerant through said inner lumen of said flexible coaxial catheter;

cooling blood in said feeding artery by contact with said cooled flexible heat transfer element; and cooling the heart of the patient by flow of said cooled blood through said feeding artery.

\* \* \* \* \*

UNITED STATES PATENT AND TRADEMARK OFFICE
CERTIFICATE OF CORRECTION

PATENT NO. : 6,149,677
DATED : November 21, 2000
INVENTOR(S) : Dobak, III

It is certified that error appears in the above-identified patent and that said Letters Patent is hereby corrected as shown below:

Title page, "Attorney, Agent, or Firm—Gerald W. Spinkle" should be "Attorney, Agent, or Firm—Gerald W. Spinks"

Signed and Sealed this

First Day of May, 2001

Attest:

NICHOLAS P. GODICI

Attesting Officer      *Acting Director of the United States Patent and Trademark Office*